United States Patent [19]

Fogarty et al.

[11] Patent Number: 4,606,347
[45] Date of Patent: Aug. 19, 1986

[54] INVERTED BALLOON CATHETER HAVING SEALED THROUGH LUMEN

[75] Inventors: Thomas J. Fogarty, 770 Welch Rd., Palo Alto, Calif. 94305; James C. Finn, III, Stanford; Thomas B. Kinney, Mountain View, both of Calif.

[73] Assignee: Thomas J. Fogarty, San Mateo, Calif.

[21] Appl. No.: 763,639

[22] Filed: Aug. 8, 1985

Related U.S. Application Data

[63] Continuation of Ser. No. 478,708, Mar. 25, 1983, abandoned.

[51] Int. Cl.$^4$ .............................................. A61M 29/02
[52] U.S. Cl. .................................. 128/344; 604/167; 604/102; 604/271
[58] Field of Search ............... 128/328, 348.1, 341, 128/344, 656–658, 1 R, 4; 604/96, 102, 167, 103, 157, 158, 159, 271

[56] References Cited

U.S. PATENT DOCUMENTS

| | | | |
|---|---|---|---|
| 3,178,732 | 4/1965 | Stibitz | 604/271 |
| 3,253,594 | 5/1966 | Matthews et al. | 604/96 |
| 3,402,710 | 9/1968 | Paleschuck | 128/1 R |
| 3,409,016 | 11/1968 | Foley | 128/344 |
| 3,433,214 | 3/1969 | Silverman | 604/104 |
| 3,506,011 | 4/1970 | Silverman | 604/158 |
| 3,525,329 | 8/1970 | Zeimer | 604/104 |
| 3,853,127 | 12/1974 | Spademan | 604/167 |
| 3,911,927 | 10/1975 | Rich et al. | 604/271 |
| 4,321,915 | 3/1982 | Leighton et al. | 128/4 |
| 4,324,262 | 4/1982 | Hall | 128/328 |
| 4,403,612 | 9/1983 | Fogarty | 128/348.1 |
| 4,467,816 | 8/1984 | Schlüter | 128/344 |
| 4,530,698 | 7/1985 | Goldstein et al. | 604/271 |

OTHER PUBLICATIONS

IBM Technical Disclosure Bulletin, vol. 10, No. 12, May 1968.

Primary Examiner—C. Fred Rosenbaum
Assistant Examiner—Gene B. Kartchner
Attorney, Agent, or Firm—Limbach, Limbach & Sutton

[57] ABSTRACT

A balloon catheter of the linear eversion type is provided with a sealed through lumen which will pass guide wires and other objects without disturbing the sealed nature of the balloon system.

9 Claims, 20 Drawing Figures

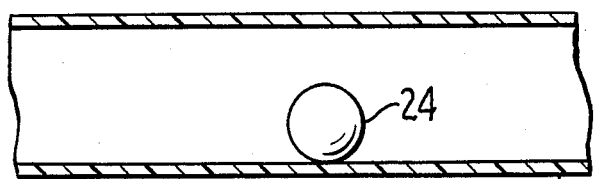
FIG.7.
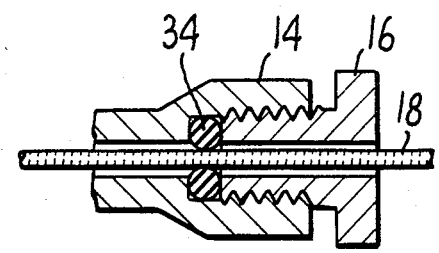
FIG.10.
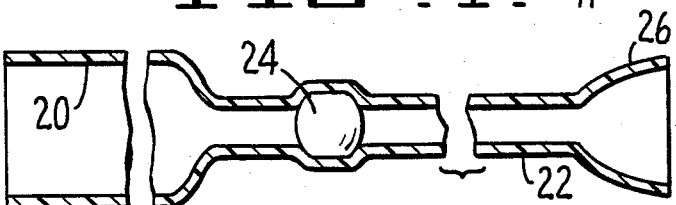
FIG.8.
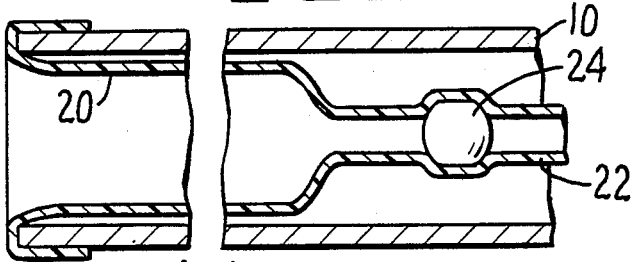
FIG.9.
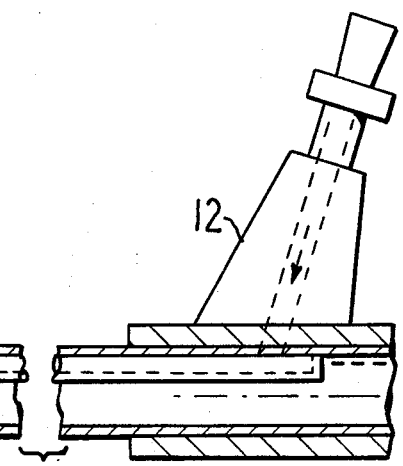
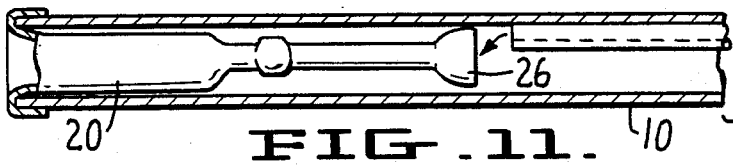
FIG.11.
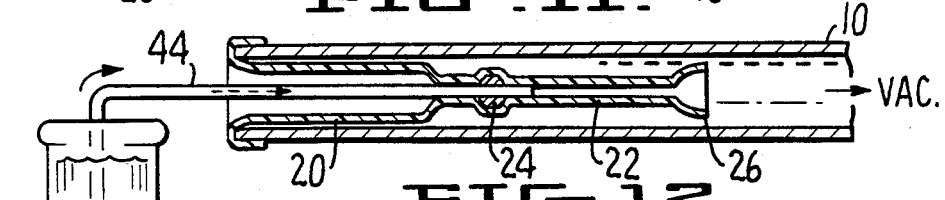
FIG.12.
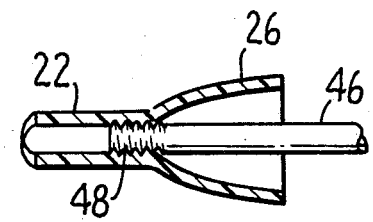
FIG.14
FIG.13.
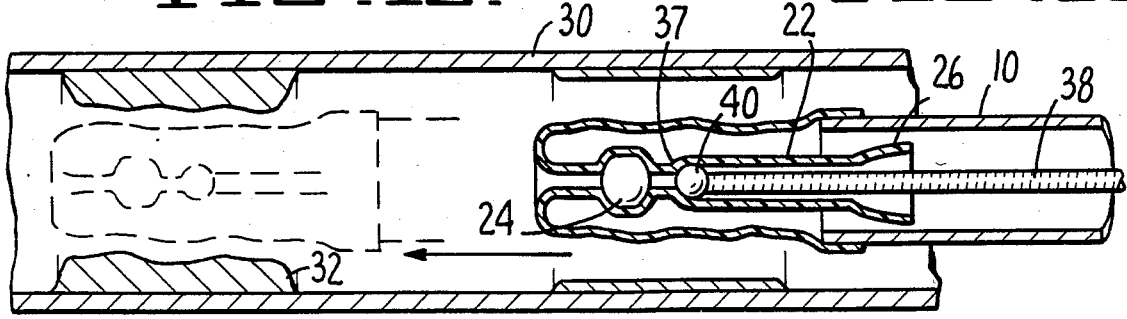
FIG.15.

INVERTED BALLOON CATHETER HAVING SEALED THROUGH LUMEN

This is a continuation of application Ser. No. 478,708, filed Mar. 25, 1983, now abandoned.

BACKGROUND OF THE INVENTION

1. Field of the Invention

The field of the invention is dilatation catheters having evertable-invertible balloons for dilating strictures or stenoses of tubular elements and passageways of the body. More specifically, the field of the invention is the provision in such catheters of a central through lumen provided with means enabling the passage through the balloon of a guide wire or other element while providing a sealed balloon system at all times.

2. Description of the Prior Art

In the dilatation catheter art, it is old to provide such catheters with evertable-invertible balloon elements. Attention is directed to U.S. Pat. No. 4,254,774 in this regard. Such balloon catheters, however, have not, insofar as we are aware, been provided with sealed through lumens enabling the passage through the balloons of guide wires and other instruments.

SUMMARY OF THE INVENTION

The essential object of the invention is to provide a balloon catheter of the evertable-invertible type with a means for passing an object, such as a guide wire or a cannula, through the balloon while maintaining a sealed balloon system.

This is accomplished, in a preferred way, by providing the free end of the balloon with a small axial elastomeric plug and providing the plug with a normally closed passageway such as one formed by pushing a needle through the plug and by then withdrawing the needle. When the balloon is subjected to inflation pressure the plug acts as an imperforate part of the balloon whether or not a guide wire or the like is extending through the plug.

DESCRIPTION OF THE DRAWINGS

FIG. 2 is an enlarged view in diametral cross-section of said catheter.

FIG. 7 is a view of tube and plug elements prior to their securement together, the tube being shown in diametral section.

FIG. 8 is a view of the balloon and plug assemblage prior to the attachment of the assemblage to the catheter.

FIG. 9 shows the assemblage of FIG. 8 in attached relation to the catheter and in inverted position therein.

FIG. 10 is a detail view in diametral cross-section of a sealing means which may be employed at the proximal end of the catheter to maintain the balloon pressurized while a guide wire extends through the catheter.

FIG. 11 is a view showing a form of purging system which may be employed with the catheter.

FIG. 12 shows another form of purging system which may be employed with the catheter.

FIG. 13 illustrates a means for inverting the balloon.

FIG. 14 shows a modified form of balloon inversion means.

FIG. 15 shows how the catheter may be moved from one stenosis to another without inverting the balloon.

DESCRIPTION OF THE PREFERRED EMBODIMENTS

Figure 1:
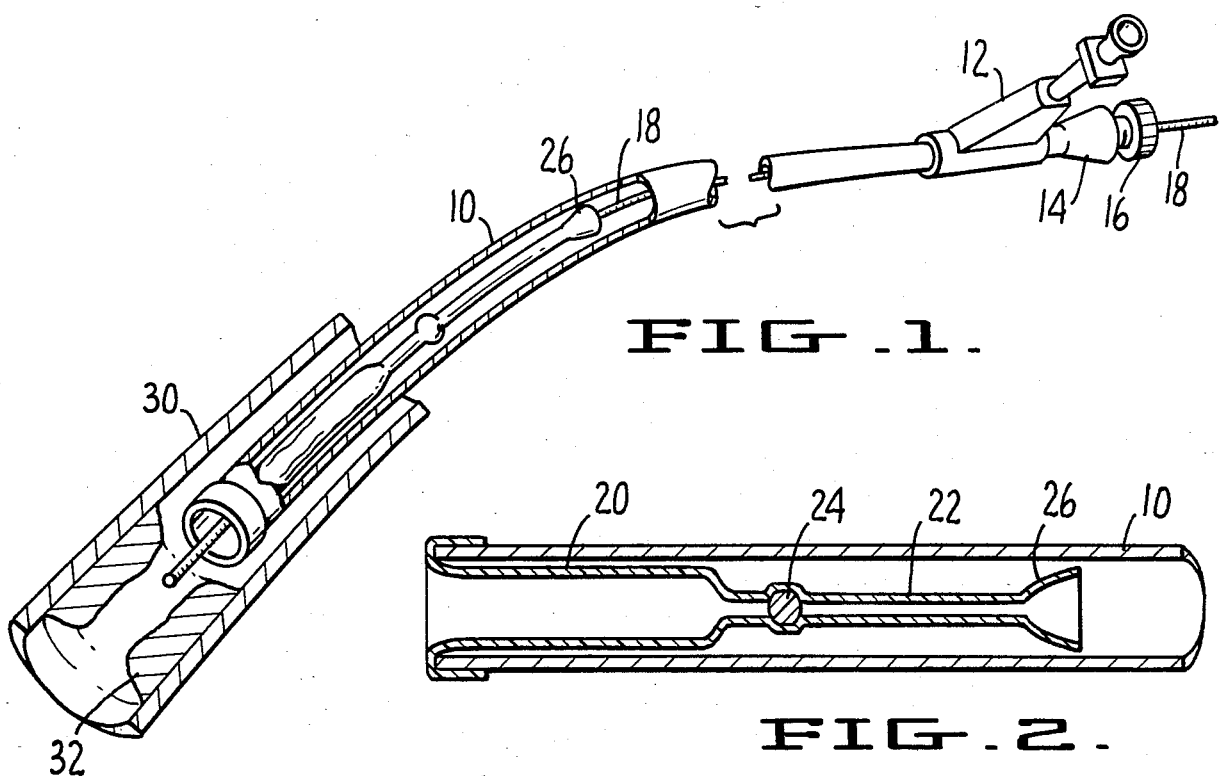
FIG. 1 is a view in perspective of a preferred embodiment of the catheter of the invention.

The catheter of FIGS. 1–15 comprises a flexible tubular body 10, fluid feed fitting 12, hub 14, screw plug 16, guide wire 18, balloon 20, balloon tubular extension 22, plug 24 and funnel-like end 26 formed on extension 22. The end of the balloon is folded over the distal end of tube 10 and sealingly secured thereto.

FIGS. 7–9 illustrate the preferred way of making the balloon and balloon extension assemblage. The plug 24 (FIG. 7) of elastomeric material, such as silicone adhesive/sealer, is pierced axially with a needle which is then withdrawn, thereby forming a normally closed or sealed passageway 28 through the seal. The plug is then placed within a tube 11 of polyethylene or other suitable material for an expansible non-elastic balloon. By heat treatment the tube is caused to shrink in the region surrounding and adjacent to the plug so as to form the shape of the assemblage shown in FIG. 8. The plug is gripped and embraced by the containing tube, or extension 22. The assemblage is then secured to the tube 10, as shown in FIG. 9.

Figure 3:
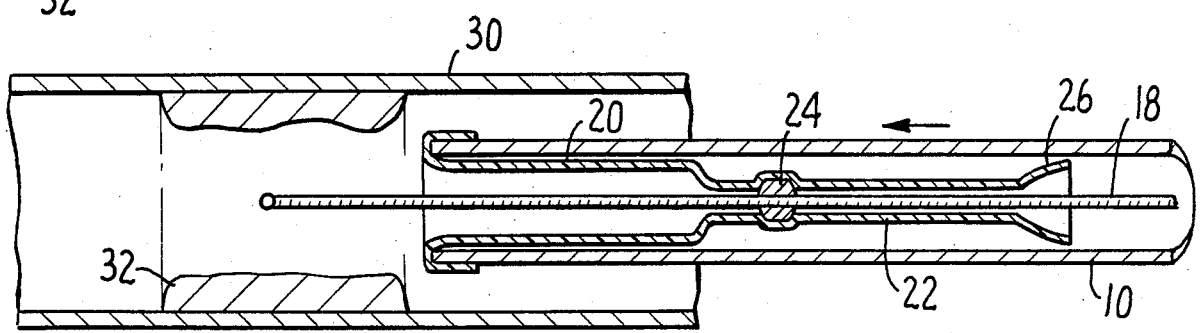
FIG. 3 is a similar view showing the catheter strung on a guide wire and positioned adjacent a stenosis to be treated.
Figure 4:
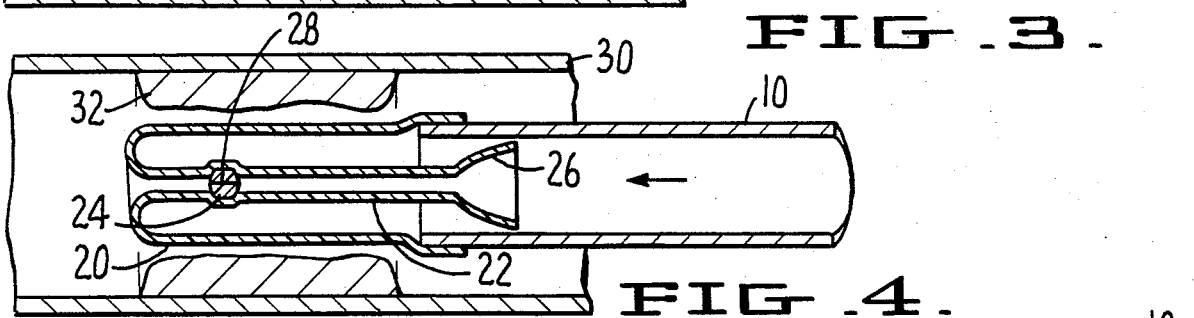
FIG. 4 is a similar view showing the balloon everted and within the stenosis.
Figures 5, 6:
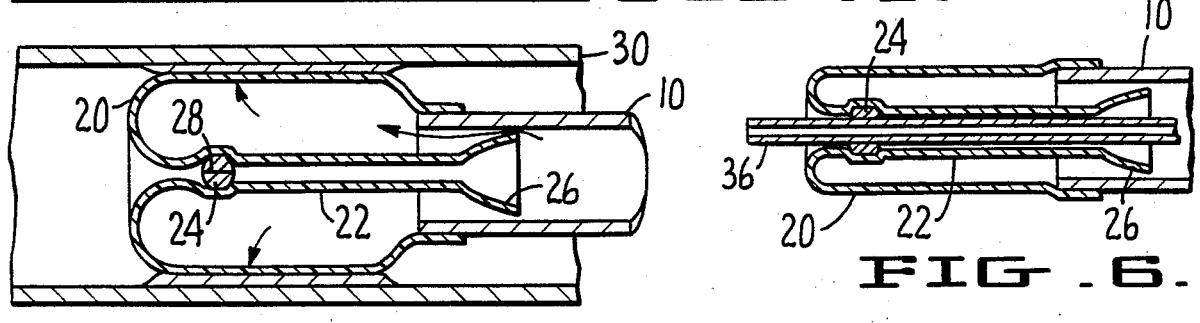
FIG. 5 is a similar view showing the balloon inflated to dilate the stenosis.
FIG. 6 is a similar view showing an open ended tube extending along the lumen of the catheter.

30 is an artery or other body tube having a stenosis or stricture 32. The sequence of usage of the catheter to accomplish dilatation of the stenosis 32 is shown in FIGS. 3–5. The catheter is threaded along guide wire 18 which traverses the plug passageway 28 and the entire catheter. When the distal end of the catheter is positioned adjacent stenosis 32, the guide wire is preferably withdrawn from the balloon and balloon extension assemblage 20, 22. The wire may remain in the proximal end of the catheter to serve as part of a sealing means (FIG. 10) comprising wire 18, compressible O-ring 34 and screw plug 16 to compress ring 34 into sealing and gripping relation with wire 18.

Inflation fluid is then injected through fitting 12 to cause eversion of the balloon into stenosis 32, as shown in FIG. 4. After balloon eversion, the balloon is further inflated to expand radially and dilate the stenosis, as shown in FIG. 5. During all this inflation activity, the plug passageway 28 remains in its normally closed position. The balloon and balloon extension are thereby provided with a sealed through lumen.

Regardless of the condition of the balloon, whether it is inverted, everted or radially inflated, thin, tubular elements, such as 36 in FIG. 6, may be passed through the plug. The tube 36 may be then used to monitor pressure conditions at the distal tip of the catheter; it may be used for the delivery of diagnostic or therapeutic substances to the distal end of the catheter; it may be used for the sampling of body fluids, such as blood; and it may be used for the passage of instruments or tools through the catheter, such as temperature monitors or fiber optic cords.

FIG. 15 illustrates how the catheter may be moved from one stenosis to another without bothering to first invert the balloon. For this purpose the extension 22 is preferably provided with a step 37. A stylet 38 having a round or flat tip 40 is inserted into the extension to abut the step. The catheter tube or body 10 and stylet 38 are then jointly moved to position the everted balloon within the next adjacent stenosis 32.

FIGS. 11 and 12 illustrate two purging systems for the catheter. In FIG. 11 the catheter is provided with a purge lumen through which purge liquid is passed to the interior of the catheter through fitting 12. When the catheter has been filled with the purge liquid, issuance of liquid through a bleeder valve, not shown, indicates that all of the air has been purged from the catheter. In FIG. 11 the purge liquid is introduced into the catheter through a needle-like fitting 44 which extends through plug passageway 28. Coupling of the proximal end of the catheter to a vacuum source causes the catheter to be filled with purge fluid.

FIGS. 13 and 14 illustrate a retraction means to reinvert the balloon. Extension 22 may have tube 46 frictionally fitted within the end thereof. When the tube 46 is pulled to the right, the balloon becomes re-inverted. As shown in FIG. 14, the tube or rod 46 may have a threaded end 48. The corresponding threads in extension 22 may be pre-formed or formed by self-threading.

Figure 16:
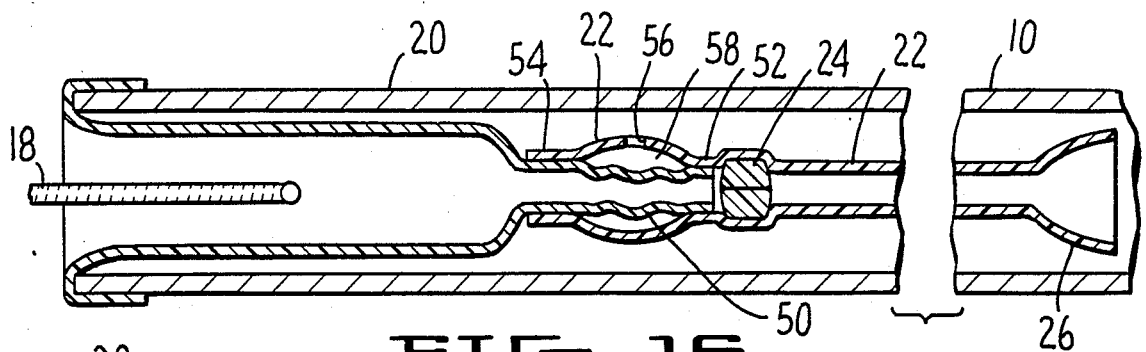
FIG. 16 is a view in diametral section of another embodiment of the catheter.
Figure 17:
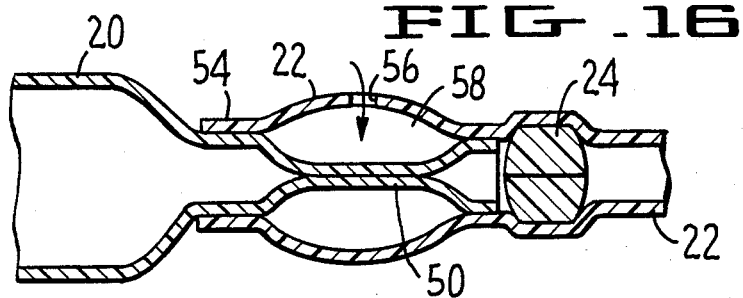
FIG. 17 is an enlarged detail view illustrating how the lumen sealing means of this embodiment operates.

A further embodiment of the catheter is shown in FIGS. 16-17. Between the plug 24 and balloon 20, extension 22 encloses a length 24 of elastomeric tubing 50. One end of this tubing is bonded to the extension 22 in the region 52. The other end of tubing 50 may be integral with the end of the balloon 20. Extension 22 is bonded to the balloon in the region 54. Extension 22 is provided with aperture 56 in overlying relation to tube 50. When inflation liquid is introduced into the catheter, the liquid enters chamber 58 between extension 22 and the tube 50 to compress the latter and close the passage along tube 50, as illustrated in FIG. 17. Further application of inflation liquid causes eversion of the balloon, and still further application of inflation liquid produces radial expansion of the balloon. The longitudinal passage through tube 50 remains closed under the effect of inflation liquid pressure during all of these operations.

Figure 18:
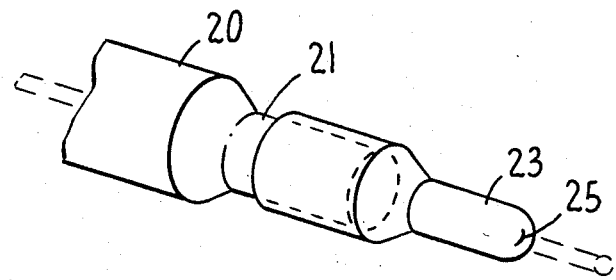
FIG. 18 is a view in perspective of the distal end of still a further embodiment of the subject catheter.
Figure 19:
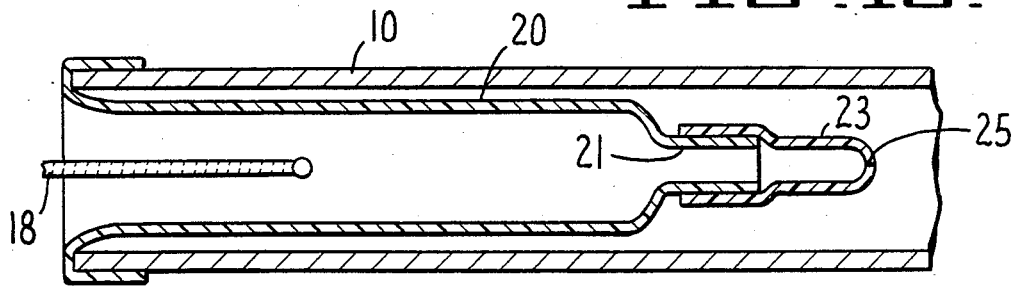
FIG. 19 shows the distal end of the catheter of FIG. 18 with the balloon being in inverted position.
Figure 20:
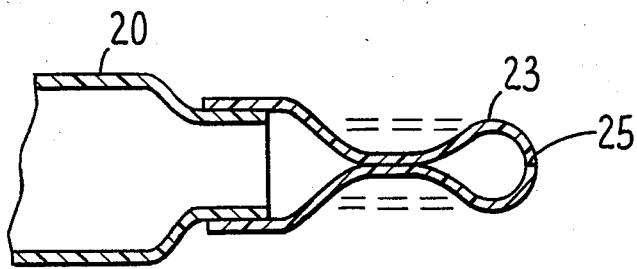
FIG. 20 is a view illustrating the sealing action which occurs when the catheter of FIG. 19 is subjected to balloon-inflating pressures.

A further embodiment of the catheter is shown in FIGS. 18-20. Here the balloon 20, preferably made of polyethylene, is provided with an open end 21 of reduced diameter. A collapsible elastomeric balloon 23 is sleeved over end 21 and bonded thereto. The balloon 23 is provided with a selfclosing hole or slit 25. When inflation liquid pressure is applied to the balloons 20 and 23, the balloon 23 collapses to form a seal and close off the interior of the catheter from the exterior thereof.

In the embodiment of FIGS. 16 and 17, the guide wire 18 may be passed through the sealed through lumen in either direction, while in the embodiment of FIGS. 18-20 such passage must be made from the distal end of the catheter in order to avoid collapsing of the balloon 23.

It is to be pointed out that the elastomeric plug 24 of the embodiments of FIGS. 1-17 can be fixed in place in various ways. The preferred way, as disclosed, is to shrink the containing tube partially around the ends of the plug, thereby mechanically bracing the plug in position. The plug can be adhesively secured to the containing tube, either with or without the mechanical bracing relationship between tube and plug.

All of the above-described embodiments allow placement of the catheter body over a guide wire which has previously been manipulated into the desired lumen or space. This provides important advantages over previous linear extrusion catheters which are incapable of being used directly over a guide wire and must be positioned with a guiding catheter, if that is possible, or without any guide or aid at all. The expertise which physicians have in placing guide wires, particularly in the cardiovascular and urological systems, makes this wire-compatibility feature of particular importance.

The catheter embodiments of FIGS. 1-17 allow replacement of the guide wire after balloon extrusion, or eversion, if desired, simply by pushing the guide wire back through the seal and past the limit of balloon eversion and then by withdrawing the catheter over the guide wire (i.e., guide wires or other thin objects may be passed in either direction through the seal). The physician can thereby easily maintain guide wire access to a difficultly reached lumen or space if further procedures or measurements are required in that space or another space which is reached through it. The present catheter provides these advantages while maintaining the advantages of the linear extrusion catheter.

What is claimed is:

1. A dilatation catheter comprising a flexible catheter body, a balloon attached to the distal end of said body and inverted within said body, means including a tubular extension attached to said balloon defining a through lumen, closure means within said lumen operable to maintain said balloon in sealed condition for eversion and subsequent radial expansion, said closure means being closed in the absence of any element passing therethrough and being penetrable by a guide wire, thin cannula, or other thin element, to provide a passage sealed in slidable engagement therewith without loss of the sealed condition of said balloon and functioning to maintain the sealed condition upon removal of such element therefrom.

2. The catheter of claim 1, said extension having a funnel-like element at its distal end to guide said wire, thin cannula, or other thin element into said lumen.

3. The catheter of claim 1, said closure means comprising an elastomeric plug secured transversely to said extension in blocking relation to said lumen, said plug having a normally closed, puncture-like axial passageway therein adapted to yieldingly accommodate said wire, thin cannula, or other thin element without loss of the sealed condition of said balloon.

4. The catheter of claim 3, said extension having a funnel-like element at its distal end to guide said wire, thin cannula, or other thin element into said lumen.

5. The catheter of claim 3, said plug fitting within a radially enlarged portion of said extension and being secured in place between radially diminished portions of said extension.

6. The catheter of claim 3, said closure means further comprising an elastomeric sleeve within said extension, said sleeve having one end fixedly attached to said balloon and the other end fixedly attached to said plug, said extension having an aperture which provides communication for the application of balloon-eversion fluid pressure to an annular chamber between said extension and said sleeve to thereby collapse said sleeve upon itself and seal said lumen against fluid flow.

7. The catheter of claim 6, said extension having a funnel-like element at its distal end to guide said wire, thin cannula, or other thin element into said lumen.

8. The catheter of claim 1, said tubular extension having its proximal end secured to said balloon and having its distal end closed except for a puncture-like normally closed passageway extending therethrough, said tubular extension being collapsible upon itself upon the application thereto of balloon-eversion fluid pressure to seal said lumen against fluid flow.

9. A method of providing the balloon of a dilatation catheter of the eversible-invertible balloon type with a sealed through lumen to enable said catheter to be moved along a guide wire while maintaining a sealed ballon system, said method comprising the steps of initially forming said balloon with an axial opening at its distal end, sealing said opening with an elastomeric plug which has been formed with a axial passageway normally closed in the absence of any element passing therethrough and adapted to accommodate the passage of a guide wire therethrough while maintaining said balloon system in a sealed condition.

* * * * *